(12) United States Patent
Seong et al.

(10) Patent No.: US 8,845,801 B2
(45) Date of Patent: Sep. 30, 2014

(54) BONE CEMENT AND METHOD (75) Inventors: Wook-Jin Seong, Roseville, MN (US);
Young Cheul Heo, Roseville, MN (US);
Hyeon Cheol Kim, Busan (KR); Iel Yong Sung, Ulsan (KR); Soo Cheol Jeong, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 149 days.

(21) Appl. No.: 13/519,822

(22) PCT Filed: Dec. 29, 2010

(86) PCT No.: PCT/US2010/062417
§ 371 (c)(1),
(2), (4) Date: Jun. 28, 2012

(87) PCT Pub. No.: WO2011/082258
PCT Pub. Date: Jul. 7, 2011

(65) Prior Publication Data
US 2013/0104771 A1 May 2, 2013

Related U.S. Application Data

(60) Provisional application No. 61/291,006, filed on Dec. 30, 2009.

(51) Int. Cl.
*A61L 24/02* (2006.01)
*A61F 2/28* (2006.01)
*C04B 7/02* (2006.01)
*C04B 11/00* (2006.01)
*A61L 24/08* (2006.01)
*A61K 6/00* (2006.01)
*A61L 24/00* (2006.01)

(52) U.S. Cl.
CPC ............... *A61K 6/0023* (2013.01); *A61L 24/08* (2013.01); *A61L 24/02* (2013.01); *A61L 24/0057* (2013.01)

USPC ............ 106/35; 106/729; 106/732; 106/735; 106/782; 623/23.62

(58) Field of Classification Search
USPC .......... 106/35, 729, 732, 735, 782; 623/23.62
See application file for complete search history.

(56) References Cited

U.S. PATENT DOCUMENTS

| 5,614,206 | A | 3/1997 | Randolph et al. |
| 5,958,131 | A * | 9/1999 | Asbridge et al. .............. 106/718 |
| 6,224,635 | B1 | 5/2001 | Ricci et al. |
| 6,607,592 | B1 * | 8/2003 | Ceccaldi ....................... 106/732 |
| 7,244,301 | B2 | 7/2007 | Axen et al. |
| 2003/0159618 | A1 | 8/2003 | Primus |
| 2003/0220414 | A1 | 11/2003 | Axen et al. |
| 2006/0213395 | A1 | 9/2006 | Lu et al. |
| 2007/0098811 | A1 | 5/2007 | Lu et al. |

FOREIGN PATENT DOCUMENTS

| WO | WO-99/32066 A1 | 7/1999 |
| WO | WO 2010/034938 | * 4/2010 |

OTHER PUBLICATIONS

Translation for WO 2010034938, Apr. 2010.*
"International Application Serial No. PCT/US2010/062417, International Preliminary Report on Patentability mailed Jul. 12, 2012", 6 pgs.
"International Application Serial No. PCT/US2010/062417, International Search Report mailed Sep. 23, 2011", 3 pgs.
"International Application Serial No. PCT/US2010/062417, Written Opinion mailed Sep. 23, 2011", 4 pgs.

* cited by examiner

*Primary Examiner* — Carol M Koslow
(74) *Attorney, Agent, or Firm* — Schwegman Lundberg & Woessner, P.A.

(57) ABSTRACT

Bone cements and methods provided include a bone cement composition having collective attributes and properties desirable for initial fixation as well as interventional applications. Compositions include an amount of Portland cement and an amount of calcium sulfate.

14 Claims, 3 Drawing Sheets

BONE CEMENT AND METHOD

RELATED APPLICATIONS

This patent application is a nationalization under 35 U.S.C. §371, and claims the benefit of priority of PCT/US2010/062417 filed Dec. 29, 2010 and published as WO 2011/082258 A2 on Jul. 7, 2011, which claims the benefit of priority to U.S. Provisional Patent Application Ser. No. 61/291,006, filed Dec. 30, 2009, the entire contents of which are incorporated herein by reference.

TECHNICAL FIELD

Various embodiments described herein relate to apparatus, systems, and methods associated with bone cements. Specifically, embodiments are described that relate to dental applications of bone cements.

BACKGROUND

Successful and predictable rehabilitation of missing teeth with dental implants has been reported in hosts with normal bone volume and density. Two remaining areas where improved techniques and materials are sought include: (1) implant failures in low density/volume bone typically found in elderly and/or medically compromised patients, and (2) peri-implantitis as a complication of dental implant procedures.

A study on Branemark implants found that only 3% of implants placed in type 1, 2 and 3 bone were lost after 5 years, while in type 4 bone, which is low density bone, failure rates were 35% over the same period. Lack of dense cortical bone and the sparse existing hard trabecular bone can fracture during surgical drilling. Self-threading dental implants can also be unstable in this type of bone. The poor healing and bone producing capacity of elderly and/or medically compromised patients further reduces implant success rates.

Figure 1:
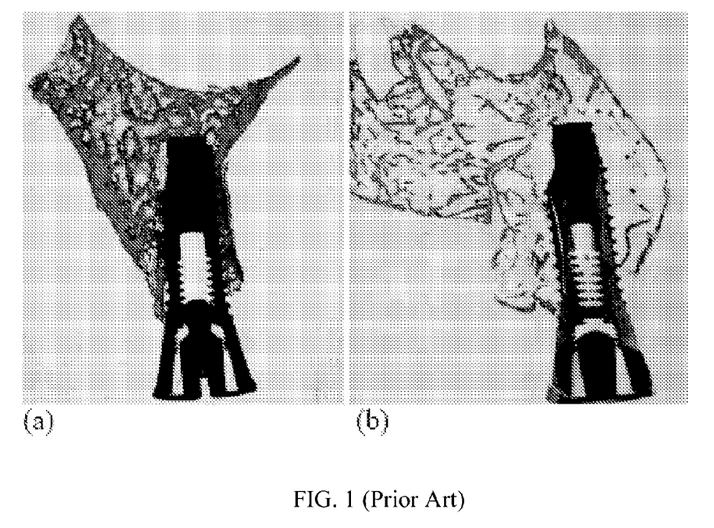
FIG. 1 shows dental implants in different types of bone according to the prior art.

FIG. 1 shows undecalcified slides of an 85-year old male fresh cadaver. The slide in (a) shows a dental implant in anterior maxilla with intimate contact to the cortical bone. The slide in (b) shows a dental implant in posterior maxilla (type 4 bone) and shows thin cortical bone and sparse trabecular bone around the implant. Implants placed in weak bone like this (b) often do not achieve initial stability and tend to fail more frequently.

When initially unstable implants are encountered, dental surgeons can replace unstable implants with wider implants provided there is enough resident bone available for this. In many cases this technique fails because available bone is hard but weak. Consequently, wider implants can lead to fracture of surrounding trabeculae, thereby causing another unstable implant situation. In loose implants, interfacial micromotion greater than 100 to 150 µm induces soft tissue formation instead of bone formation around implants, which is regarded as a failure.

In addition to mechanical issues with dental implants, peri-implantitis can be a significant problem for dental implant recipients, as can it's analog, periodontitits, for natural teeth. Peri-implantitis and periodontitis are characterized by inflammation of the mucosa and loss of supporting bone. These conditions can lead to complete loss of osseointegration and implant or tooth loss.

A few selected examples of shortcomings of existing procedures and bone cements have been listed. There exists a need for improved bone cements that address these, and other issues of existing bone cements. In particular, in the dental field, there exists a need for dental implant cement compositions which can physically fortify existing bone and repair previously applied failing dental implants in recipients.

DETAILED DESCRIPTION

In the following detailed description of the invention, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized and structural, compositional, etc. changes may be made.

As used herein, the term "comprising" means the elements recited, or their equivalent in structure or function, plus any other element(s) which are not recited. The terms "having" and "including" are also to be construed as open ended unless the context suggests otherwise. Terms such as "about," "generally," "substantially" and the like are to be construed as modifying a term or value such that it is not an absolute, but does not read on the prior art. Such terms will be defined by the circumstances and the terms that they modify are understood by those of skill in the art. This includes at the very least the degree of expected experimental error, technique error, and instrument error for a given technique used to measure a value.

Composition embodiments of the invention may be formulated for dental applications. The phrase "formulated for dental application" refers to the collective attributes and properties desirable for the reinforcement and interventional uses as resulting from the particular combination of ingredient and their relative amounts and proportions. The desirable collective attributes and properties include, but are not limited to, rapid setting time, optimal viscosity (moldable (e.g. condensable) or injectable depends on its application), biocompatibility/low cytotoxicity, osteoconductivity/osteoinductivity, high sealing capacity, improved resiliency, adequate load-bearing capacity and long-term fatigue resistance.

As used herein, the term "hydraulic," when used to define the composition of the invention, refers to the attribute of being hard-setting or capable of setting in water-based or aqueous environments.

In one embodiment of the invention, a bone cement composition is described. In selected examples, bone cements described are used in dental applications, although the invention is not so limited.

One example of a bone cement composition includes: a) Portland cement; b) calcium sulfate; c) carbon fiber; and d) hydroxyethyl cellulose. Another example of a bone cement composition includes: a) Portland cement; b) calcium sulfate; and d) hydroxyethyl cellulose. Another example of a bone cement composition includes: a) Portland cement; and b) calcium sulfate.

One example of a cement composition according to the invention is as follows:

| Ingredient | Amount (g) | Amount (% by weight) |
|---|---|---|
| Portland cement | 20 g | 65.93% |
| $CaSO_4$ | 10 g | 32.97% |
| Carbon fiber | 0.084 g | 0.28% |
| Hydroxyethyl cellulose | 0.25 g | 0.82% |
| Total: | | 100.0% |

As shown in the table above, a majority of components by weight include approximately ⅔ Portland cement and ⅓ calcium sulfate (approximately 66% Portland cement and 33% calcium sulfate). In another example, dry components, as listed above, include calcium sulfate in a range from 10% to 35% dry weight. In another example, dry components, as listed above, include calcium sulfate in a range from 14% to 20% dry weight. In another example, dry components, as listed above, include calcium sulfate at approximately 15% dry weight, with Portland cement comprising approximately 85% with possible additions of other components such as hydroxyethyl cellulose, or carbon fiber, etc. in smaller percentage ranges.

In one example, a matrix phase and a dispersed phase are formed in a bone cement after curing. In the example shown in the table above, the Portland cement, calcium sulfate, and hydroxyethyl cellulose, when mixed with water, form a matrix phase, and the carbon fiber forms a dispersed phase.

The addition of dispersed phases provides additional enhancement of mechanical properties in selected embodiments. Although carbon fiber is noted as an example of a dispersed phase, the invention is not so limited. Other materials in fiber, or other form, may be used as a dispersed phase in the bone cement. In other embodiments, dispersed phase components are not used.

Calcium sulfate acts as an accelerant to the Portland cement. reducing a curing time of a pure Portland cement from a number of hours to a number of minutes in bone cements embodiments of the present invention.

In selected embodiments, the addition of hydroxyethyl cellulose provides cohesion properties to the bone cement that aid in workability or moldability prior to curing of the cement. The addition of hydroxyethyl cellulose can further prevent washing away of bone cement due to liquid flow such as bleeding.

Water is added to bone cement compositions described, to activate the components, and begin a setting process of the cement. In one example method, an amount of water is adjusted to select a desired viscosity of the bone cement, while in the working stage of applying the bone cement. In selected embodiments, an amount of water is selected to provide a moldable consistency such as putty. In this state, the bone cement is easy to work with, and will squeeze into crevices of the adjacent bone during application, yet will not flow away from the site during curing. In one example, an amount of water is added to provide a viscosity that is injectable from a hypodermic or other suitable application device. In selected procedures, it may be desirable to have the bone cement injectable.

In one example, water is added to dry components in a weight fraction of approximately 0.3 (for example 3 ml of water for 10 grams of dry components). In one example a weight fraction of 0.3 produces a condensable viscosity. In one example, water is added to dry components in a weight fraction range between 0.3 and 0.5. In one example a weight fraction of 0.4 produces a flowable viscosity suitable for injection.

Additional ingredients can be added to the composition of the invention provided such do not substantially interfere with or compromise the chemical and physical attributes associated with the invention.

Existing bone cements and fillers with modifiers are typically designed to be resorbable, and contain components to encourage new bone growth. However, amorphous biological modifiers such as BMP (bone morphogenic protein) or PDGF (platelet-derived growth factor) do not afford mechanical support for implants.

Other existing fillers utilize resorbable particulated bone, such as cadaveric or bovine bone. The bone particles are hard, and can induce further fracture of relatively weak trabecular bone when applied into a loose bone socket, with subsequent implant insertion—typically by rotation of a threaded implant base. Embodiments of the present invention avoid problems with particulated bone by adjusting a viscosity of the bone cement, and/or not-having large hard particles. A less viscous bone cement flows into crevices and around implants more effectively, and reduces unwanted breakage of adjacent bone.

Calcium phosphate-containing cement is known for its biocompatibility and mimicking of hydroxyapatite, resorbability and molding capabilities. However, it is slow-setting, easily washed away until cured, and has a relatively weak tensile strength, thereby limiting its suitability for anatomical stress-bearing contexts. Bone cement compositions of the present invention provide strength (for example, to support long-term chewing), faster setting times and better adhesion to adjacent bone due to its hydrophilic properties.

Orthopedic surgeons typically remove trabecular bone prior to applying polymethylmethacrylate (PMMA) cement to stabilize hip or knee implants to avoid the likelihood of implant loosening within, and PMMA cement fracturing of, weaker trabecular bone. However, in contrast to bone cement compositions of the present invention, PMMA is hydrophobic, and does not adhere well to wet bone. When applying PMMA cements to areas where bleeding is occurring, the blood may prevent the cement from forming a strong bond with the bone due to the hydrophobic nature of PMMA. Using bone cements of the present invention, the hydrophilic properties not only facilitate a strong bond in the presence of blood or water, but bone cement of the present invention provide an aid in stopping bleeding.

As discussed above, one ingredient in the composition of the invention comprises Portland cement. A high sealing capacity and high pH (highly basic) of Portland cement may play important roles in intervening peri-implantitis and periodontitis by eradicating bacteria in an infra-bony pocket formed by the progression of bone loss around an ailing dental implant or tooth. Portland cement will decontaminate the implant surface well, with a high pH during the hardening process, and maintain a perfect seal so no bacteria left on the implant surface can survive. With great sealability, osteoconductivity, and adequate mechanical strength, embodiments of bone cement described can maintain a long-term stable bone-cement-implant architecture which will resolve peri-implantitis/periodontitis and also prevent re-infection, prolonging the life of the once-compromised implant or tooth.

In general, Portland cement clinker is a hydraulic material which contains at least about two-thirds by mass of calcium silicates ($3CaO.SiO_2$ and $2CaO.SiO_2$), and the remaining ingredients comprise aluminum and iron-containing clinker phases and other compounds. Preferably, the ratio of CaO to $SiO_2$ is not less than 2.0. In selected embodiments, the magnesium content (MgO) does not exceed 5.0% by mass.

Calcium sulfate sources include, but are not limited to, ADA Spec #25 Type I Impression plaster or Quick set plaster Type IV High strength dental stone or Improved stone and Type V high strength high expansion dental stone. Collectively, the Portland cement and calcium sulfate ingredients can be referred to as the cement powder composition.

As discussed above, in selected embodiments, additional components are added to the powder composition, or water to be mixed with the powder composition, to form one or more dispersed phases. In one example, carbon fiber and hydroxyethyl cellulose may be dispersed homogeneously in water first. In other selected examples, only hydroxyethyl cellulose may be dissolved in water first. To formulate an example dispersed phase cement, the powder ingredients are combined with a dispersed material (e.g. carbon fibers and/or hydroxyethyl cellulose) with viscosity adjusted by selecting the amount of water added to activate and prepare the final cement composition.

As discussed above, calcium sulfate functions as an accelerant and affords quick-set properties as well as bone-cement interface surface osteoconductive morphology when combined with cement. Calcium sulfate is resorbable. When employed within the composition of the invention, resorbable calcium sulfate when combined with non-resorbable Portland cement enhances the uniformity of mix and forms an exterior textured surface morphology in hardened form, which can enhance both short term and immediate structural strength as well as enhance long term osseointegration at the cement-bone interface. Calcium phosphate is used in orthopedic cements due to its chemical similarity to natural bone element profile. However, calcium phosphate cement is slower-setting, with relatively weaker strength than bone cements described in the present disclosure, and is more easily washed away by natural and introduced fluids at an implant site (e.g., blood and water). In contrast, it has been observed that calcium sulfate with Portland cement forms a condensable composition with better coherence, adherence, and residency in the presence of and despite such fluids. Also, the expansion of calcium sulfate can compensate the shrinkage of Portland cement during curing and lower the chance for crack formation.

The composition of the invention can further comprise carbon fiber. In selected embodiments, carbon fiber can be present in an amount ranging from between about 0.7 to about 0.9 percent by weight of the total composition dry weight. In selected embodiments, carbon fiber can be present in an amount ranging from between about 0.15 to about 0.35 percent by weight of the total composition dry weight. In selected embodiments, carbon fiber can be present in an amount of approximately 0.28 percent by weight of the total composition dry weight. Carbon fiber can function as a strengthening agent, and can afford the composition several advantageous attributes, including: resiliency and deformability without fracture and resistance to complete failure, simulating mechanical properties of trabecular bone that the bone cement should interface with in vivo.

In selected embodiments, hydroxyethyl cellulose can be present in the composition in an amount ranging from between about 0.2 to about 0.4 percent by weight of the total composition dry weight. In selected embodiments, hydroxyethyl cellulose can be present in the composition in an amount ranging from between about 0.1 to about 2.5 percent by weight of the water. In selected embodiments, hydroxyethyl cellulose can be present in the composition in an amount ranging from between about 0.5 to about 1.5 percent by weight of the water. In selected embodiments, hydroxyethyl cellulose can be present in the composition in an amount ranging from between about 0.8 to about 1.1 percent by weight of the water. Hydroxyethyl cellulose can function as a dispersant for the carbon fiber ingredient as well as inducing stickiness of mixed cement thus providing better coherence, adherence, and residency to the surgical site against active bleeding.

As discussed above, one of the advantages associated with the composition of the invention is the ability to vary viscosity as preferred to the contemplated application context. The composition of the invention when formulated to the appropriate or desired viscosity for application in initial fixation of a dental implant to a recipient's bone, affords the advantages of structural fortification of attenuated or structurally compromised bone. Thus, the composition of the invention in this regard can be formulated to stabilize broken bone-implant interface thereby creating a stable bone-cement-implant interface having the necessary structural integrity to support the implant under chewing. The condensable viscosity for this application can be generally greater compared to the interventional application.

Figure 4:
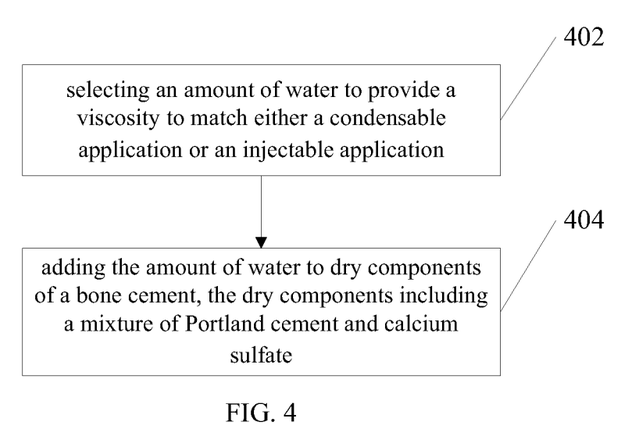
FIG. 4 shows an example method of forming a bone cement according to an embodiment of the invention.

FIG. 4 illustrates an example method of forming a bone cement. In operation 402, an amount of water is selected to provide a viscosity to match either a condensable application or an injectable application. In operation 404, the amount of water is added to dry components of a bone cement. The bone cement includes a mixture of Portland cement and calcium sulfate as described above.

Embodiments of bone cement described can be delivered into a bony socket, and can be condensed against the trabecular bone to form a hybrid zone where bone cement and trabecualae intermingle. A wide hybrid zone positioned between weak trabecular bone of the patient and bone cement works as a transition layer which prevents further fracture of the weak trabecular bone by either the bone cement or dental implant under chewing.

In the interventional application of the composition of the invention (i.e., repair of a previously introduced and currently failing dental implant which has bony pocket around the implant formed by the progressive loss of surrounding bone due to peri-implantitis), the viscosity can be adjusted to be lower in order to prepare a flowable composition that can be injected or otherwise applied between an existing implant in situ and the surrounding bone. In general, the suitable viscosity for this application is generally lower as compared to that of the fixation application described herein above.

The dental implant bone cement composition of the invention can afford the benefits of being substantially non-resorbable, optimizing intact bone structure/condition usage, and minimizing destruction of trabecular bone. Furthermore, the composition of the invention can withstand and endure the physical forces transferred to the cement and bone as applied to the dental implant by the recipient. An important aspect of the invention is the combination of the properties of the cement per se together with the interaction and function of the cement between the implant and the surrounding bone.

The following examples further illustrate the invention. None of the embodiments and techniques set forth in the examples are meant to be construed as a limitation of the invention.

EXAMPLES

Example 1

Bone-Cement-Implant Interface

Figure 2:
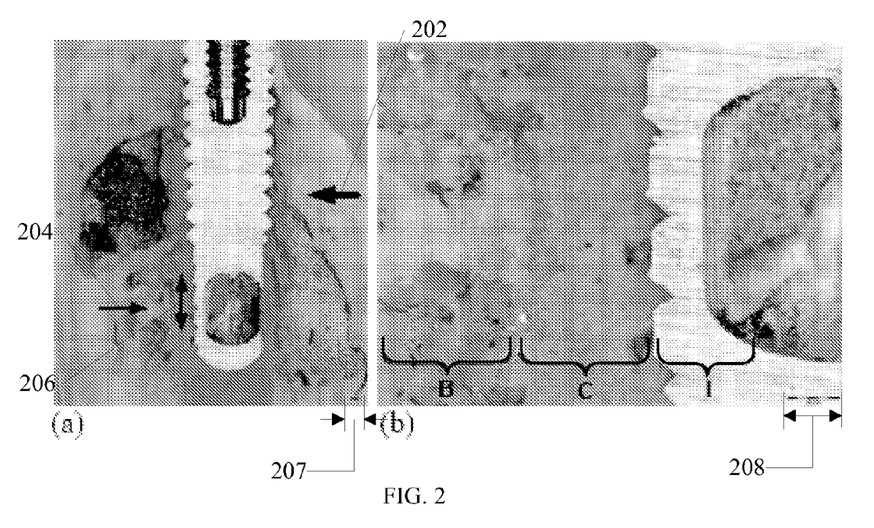
FIG. 2 shows cross sectioned bone/bone cement/implant interfaces according to an embodiment of the invention.

FIGS. 2(a) and (b) show a cross-sectional view of a calf mandible with an implant held in place with cement according to an embodiment of the invention. Arrow 202 indicates cortical bone. The thin arrow 204 indicates trabecular bone; double arrow 206 indicates cement (Reference bar 207 is 1.0 mm long). (b) Close-up view shows intimate contacts at bone (B), cement (C), implant (I) interfaces (Reference bar 208 is 200 µm long).

A 3.5 mm diameter, 10 mm long dental implant with Portland cement was placed in loosely prepared (3.7 mm) bony socket of a calf mandible. After 7 days, the implant and mandible were sectioned using a low-speed diamond blade saw to investigate bone-cement-implant interfaces as shown in FIG. 2. Highly intimate contact at the bone-cement-implant interfaces was observed. Micro-hardness tests were performed on the cross-section of the calf mandible using micro-hardness testing machine (MICROMET™ 5104 from Buehler LTD, Lake Bluff, Ill.). The Vicker's hardness was measured for the various materials as follows: cortical bone was 253 MPa, trabecular bone 40 MPa, bone cement 297 MPa, and bone-cement interface 128 MPa. Seven-day old bone cement hardness was comparable to that of cortical bone.

Example 2

Comparative Short-Term Stability

Six dental implants (3.3 mm×10 mm) were placed in the left and rights sides of a 56-year old male fresh human cadaver mandible. Three implants were placed in 3.8 mm diameter drilled bony socket with an example bone cement (Portland cement 30 g+carbon fiber 0.084 g+HEC 0.25 g+water 12 cc without calcium sulfate) and three self-threaded implants were placed in 2.8 mm bony sockets. Implant stability was then measured three times per implant with a magnetic pulse device (OSSTELL Mentor, Osstell A B, Gothenburg, Sweden) after 18 hours from cement mix time.

Figure 3:
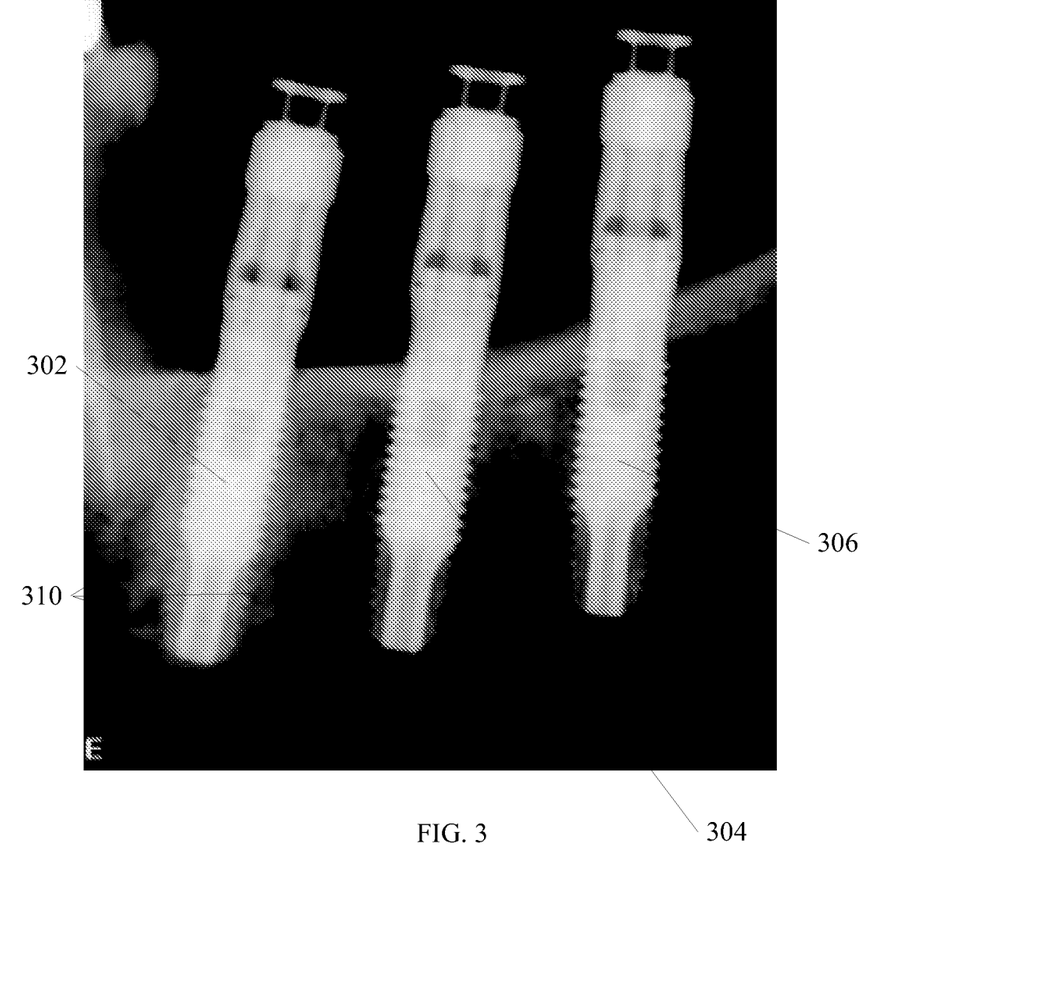
FIG. 3 shows a radiograph of implants and bone cement according to an embodiment of the invention.

FIG. 3 shows three implants placed in a left side of a mandible according to an embodiment of the invention. The left implant 302 was placed in loosely prepared socket (0.5 mm wider) with bone cement according to embodiments described in the present disclosure. The Figure shows that the bone cement further penetrated into trabecular bone making a wide hybrid zone 310. The two right implants 304, 306 were self threaded into the bone socket (0.5 mm narrower) without using bone cement. Implant stability was measured using magnetic pulse device.

Implant stability quotient (ISQ) ranges from between 1 and 100 with the higher number indicating higher stability. As for the implants described above, the average ISQ values for the three self-threaded implants were calculated at 62, 61, and 63. The average ISQ values for the implants cemented according to the invention were 63, 73 and 65.

Standard periapical radiographs of the dental implants and cement composition were taken. It was observed from the radiographs that the cement placed around the initially unstable implants penetrated into the surrounding trabecular bone to form a widened "hybrid zone" or fortified commingling of cement and trabecular bone. Such strengthening can enhance immediate implant stability subjected to load.

Example 3

Comparative Immediate Load Bearing

Compressive failure tests were performed on the six implants from Example 2 using an MTS machine (MTS 858 MINI BIONIX II from MTS Co., Eden Prairie, Minn.). Failure loads of 213 N, 216 N and 150 N were recorded for the three self-threaded implants, whereas the failure loads for cemented implants (Portland cement 30 g+carbon fiber 0.084 g+HEC 0.25 g+water 12 cc without calcium sulfate) were 110 N, 102 N and 154 N measured at 19 hours post-cement time. On average, the failure load was lower for the cemented implants as compared to the self-threaded implants. It is believed that the addition of calcium sulfate to the Portland cement composition increases its short-term strength.

Example 4

In-Vivo Implant Stability and Load Bearing

A 20 rabbit study was performed to test how strong cemented implant's bone-cement-implant interface is compared to the conventionally self-threaded implant's bone-implant interface at 1, 4, 8, and 12 weeks after the surgery. To simulate initially unstable dental implants, the bone was over-prepared 0.3 mm wider (3.6 mm) than the diameter of dental implant (3.3×8.5 mm) in the cemented implant side (left femur) while the self-threaded implant side (right femur) bone was prepared 0.3 mm narrower (3.0 mm) than the implant diameter so that implant can be self-threaded like a screw in order to achieve initial implant stability. Two implants per femur were placed in the medial side of the femur, one in distal epicondyle and another one in the cortical shaft of the femur. A bone cement with a composition of (Portland cement 20 g+calcium sulfate 10 g+carbon fiber 0.084 g+HEC 0.25 g+water 12 cc) was used in this in-vivo study.

Initial implant stability of all self-threaded implants were measured in all 4 directions using a magnetic pulse device at implant surgery. At 1, 4, 8, and 12 week sacrifices, both sides of femurs with two implants each (one implant in epiphysis and another one in cortical shaft) were extracted. After-healing stability of all implants was recorded at animal sacrifice. Initial stability measured in epiphysis of femur was higher than the one in cortical shaft, indicating bone quality of epiphysis is better than the cortical shaft's. After-healing stabilities of self-threaded and cemented implants were all similar once healing lasts 4 weeks or longer.

Initial (Primary) & After-Healing (Secondary) Stability of Implants in Rabbit Femur After Various Healing Intervals

| | Epiphysis (good bone) of femur | | | | Cortical shaft (poor bone) of femur | | | |
|---|---|---|---|---|---|---|---|---|
| Post-operation healing | Implant-bone (self-threaded) | | Implant-bone cement-bone (cemented) | | Implant-bone (self-threaded) | | Implant-bone cement-bone (cemented) | |
| | Primary S. | 2ndary S. | Primary S. | 2ndary S. | Primary S. | 2ndary S. | Primary S. | 2ndary S. |
| 1 week | 69 ± 5 | 59 ± 2 | — | 52 ± 6 | 47 ± 12 | 54 ± 6 | — | 52 ± 7 |
| 4 week | 69 ± 4 | 74 ± 6 | — | 66 ± 6 | 48 ± 13 | 68 ± 3 | — | 66 ± 6 |

-continued

| Post-operation healing | Epiphysis (good bone) of femur | | | | Cortical shaft (poor bone) of femur | | | |
|---|---|---|---|---|---|---|---|---|
| | Implant-bone (self-threaded) | | Implant-bone cement-bone (cemented) | | Implant-bone (self-threaded) | | Implant-bone cement-bone (cemented) | |
| | Primary S. | 2ndary S. | Primary S. | 2ndary S. | Primary S. | 2ndary S. | Primary S. | 2ndary S. |
| 8 week | 68 ± 4 | 66 ± 4 | — | 69 ± 7 | 58 ± 9 | 67 ± 6 | — | 69 ± 5 |
| 12 week | 71 ± 5 | 64 ± 2 | — | 68 ± 6 | 56 ± 9 | 68 ± 4 | — | 75 ± 8 |

Push-in tests at the loading rate of 0.05 mm/min were performed using MTS machine (MTS Systems Corporation, Eden Prairie, Minn.) until the implant-bone or implant-cement-bone interface is failed. The 0.2% off-set yield load and displacement at that point were recorded.

Yield Load of the Implant Interfaces in Rabbit Femur after Various Healing Intervals

| Post-operation healing | Implant-bone (self-threaded) | Implant-bone cement-bone (cemented) |
|---|---|---|
| 1 week | 199 N ± 51 | 402 N ± 51 |
| 4 week | 431 N ± 50 | 500 N ± 51 |
| 8 week | 428 N ± 51 | 464 N ± 49 |
| 12 week | 557 N ± 49 | 473 N ± 49 |

Yield load data shows that bone-cement-implant interface is stronger than bone-implant interface at all first three healing intervals (1, 4, 8 weeks), even though the cement side bony socket was prepared 0.3 mm bigger than the implant diameter at surgery to simulate initially unstable implant.

Example 5

In-Vivo Fatigue Test Using Chewing Machine

Using the same surgical protocol used in Example 4, one implant was self-threaded to the epiphysis of one side femur and another implant was cemented in 0.3 mm wider bony socket using bone cement to simulate initially unstable implant. After one week healing, a rabbit was sacrificed and the implant/femur was imbedded in resin and mounted to the chewing machine (Advanced Artificial Oral Environment, University of Minnesota, Minneapolis, Minn.). A cycle of 300,000 which is equivalent to 1-year human chewing was delivered to the cover screws of both implants and loading was set at 13.4 N in 4 Hz Implant stability after 1 week of healing was measured before and after the 300,000 cycles of chewing on both implants. Implant stability improved due to the compression of the bone and/or cement under repeated chewing and no displacement of the implant relative to the surrounding bone was recorded. From this study it can be concluded that one week healed, cemented implant with bone cement as disclosed in a loose bony socket of 0.3 mm wider than implant's diameter survived a year worth of chewing.

Example 6

Dental Implant Bone Cement Preparation and Use

As discussed above, bone cement embodiments of the present invention can be prepared differently (for example viscosity) depending on their application. One application includes rescue of an initially unstable dental implant placed in low quality jawbone, e.g., in elderly or low healing capacity patients. Another application includes intervening in the pathological condition and/or prolonging the life of an ailing implant which is losing bone surrounding the implant due to either over-loading or peri-implantitis.

A composition having the following formulation can be prepared and sterilized: Portland cement 20 g, Quick set plaster (calcium sulfate) 5 g, Improved stone (calcium sulfate) 5 g, $H_2O$ 8 to 12 cc, carbon fiber 0.084 g or 0.2% of cement (powder plus water), hydroxyethyl cellulose 0.25 g or 0.6% cement (powder plus water). Another composition without carbon fiber also can be prepared: Portland cement 8.5 g, calcium sulfate (type V high strength high expansion dental stone) 1.5 g, water 3 ml, and hydroxyethyl cellulose 0.03 g (1% of water).

The cement, fiber and hydroxyethyl cellulose can be prepared separately in plastic cups according to the weight ratio desired. Fiber (7.2 micron diameter) can be further cut into 1 to 2 mm length segments after weighing to facilitate better dispersion in the mixture. Portland cement, quick set plaster (calcium sulfate) and improved stone (calcium sulfate) can be mixed together, while fiber and hydroxyethyl cellulose can be kept separate. Each plastic cup can then be sealed with plastic wrap. Fiber and the cement powder (Portland cement, quick set plaster and improved stone) can be sterilized with ethylene oxide gas conducted at a temperature of between about 30° C. and about 60° C. with relative humidity above about 30% and gas concentration of between about 200 and 800 mg/l for a period of about at least 3 hours. After sterilization, individual cement components can be covered with extendible wrap until time of use.

Clinical Application 1: To Rescue an Initially Unstable Dental Implant

A bony socket can be prepared following standard dental implant surgical protocol using sequential drills and inserting self-threading dental implant with 15-30 rpm. If an implant is found to be unstable and surgeon's prognosis on that implant success is low after healing, the composition of the invention can be used to rescue a possible failing implant which would need to be removed immediately unless fixed with the composition. The cement composition of the invention should be available for immediate use.

The unstable implant can be removed from the bony socket and rinsed with saline to remove surface blood, and then dried with an air syringe. A tapered cover screw can be connected to the implant securely with a screw driver. Using a sterile gauge, the bony socket can be compressed to control bleeding while the cement composition is being mixed.

Sterile de-ionized water (9 cc) can be added to 0.25 g hydroxyethyl cellulose and stirred until the hydroxyethyl cellulose is completely dissolved within the water (approximately 30 seconds of stirring time). Carbon fiber (0.084 g) can then be added into the water/hydroxyethyl cellulose mixture and stirred thoroughly using a spatula until the fibers are homogenously dispersed (about 30 seconds of mixing). The cement power components (Portland cement, quick set plaster and improved stone) can be added to the cup. As the cement component is added to the cup, a spatula can be used to quickly and thoroughly mix on a vibrator until the sample is homogenous and achieves condensable consistency (about 15 to 20 seconds of mixing).

The gauze compaction can be removed and the bony socket can be exposed by the surgeon. Using a dental amalgam carrier, the surgeon carries the cement from the plate into the bony socket, and a surgical assistant can condense the cement further into the socket using amalgam plugger and a gauze on top of the cement. This procedure can be repeated until the bony socket is filled with cement with good condensation.

The retrieved dental implant can be rotated back into the bony socket where the cement composition has been applied until the tapered cover screw touches the brim of cortical bone and the implant is stabilized. After thoroughly cleaning remaining excess cement remnant from around the implant and surrounding bone, soft tissue flap can be sutured to cover the implant completely. A post-surgical x-ray can be performed and instructions dispensed to the recipient/patient.

Clinical Application 2: To Treat an Ailing Implant

Once an ailing implant which is losing bone around the implant due to either over-loading or peri-implantitis after several years of function is identified, intervention of an ailing implant with the cement composition of the invention can be planned. Advantageous sealing properties and high pH of the cement can help to eradicate the bacteria in conjunction with systemic antibiotic treatment. This may also further extend the longevity of the ailing implant. The cement composition can be initially prepared in accordance with the above description. For this application, sterilized cement composition should be ready for immediate use at the time of the procedure.

Following standard periodontal surgical protocol, full thickness flap of soft tissue can be opened to uncover implant threads and expose surrounding bone. Implant supported crown restoration can be removed and cover-screw can be connected to the implant securely. Granulation tissue surrounding the implant and occupying infra-bony socket of surrounding bone can be thoroughly removed by curette. The surface of exposed threads of dental implant can be detoxified with 10% hydrogen peroxide as the cement powder composition ingredients are being mixed.

Once the cement is prepared, 11 cc of sterile de-ionized water can be added to a 0.25 g of hydroxyethyl cellulose and the mixture can be stirred for a period of about 30 seconds until the hydroxyethyl cellulose is completely dissolved in the water. After, 0.084 g of carbon fiber can be added to the water/HEC mixture. Using a spatula, the fiber can be stirred thoroughly until homogenously dispersed within the mixture (about 30 seconds of mixing). Once the fiber has been combined with the HEC/water mixture, 30 g of cement powder composition (Portland cement, calcium sulfate from Quick-set plaster and Improved stone) can be added to the cup. As the cement is added, a spatula can be used to quickly and thoroughly mix on a vibrator until the sample is homogenous (typically about 15 to 20 seconds). The hydrated cement is dispensed into the syringe. Meanwhile, a soft tissue flap is reflected and the detoxified surface of an ailing implant and surrounding bone socket can be exposed by the surgeon. Using a syringe, surgeon injects flowable cement into the infra-bony pockets formed around the ailing implants. After placement of the cement next to the implant, a thin endodontic plugger and sterile gauze are used to pack the cement into the infra-bony pockets so that there is no empty space left in sulcus.

After cleaning extra cement remnant from the bone, implant supported crown restoration and abutment are reconnected to the implant. Soft tissue flap is sutured back around the dental implant and the occlusion of the ailing implant is carefully adjusted so that no further occlusal trauma can be applied. Post-surgical X-ray is performed and prescriptions for systemic antibiotics and 0.2% chlorhexidine digluconate rinse are given to the patient.

Additional examples uses of bone cements as described in the present disclosure include, but are not limited to the following:

1. To Stabilize Initially Unstable Implants at First Stage Implant Placement Surgery Initially unstable implants, after final insertion into the bony socket at the first stage surgery (implant placement surgery) can be removed and bone cement is mixed and condensed into the loose bony socket and same implant can be replanted into cement packed bony socket.

2. To Stabilize Unstable Implants at $2^{nd}$ Stage After Healing

Unstable implants that fail to achieve osseointegration, after 3-6 months of healing at $2^{nd}$ stage surgery, can be removed and granulation tissue lining the bony socket can be thoroughly removed. Bone cement is mixed and condensed into the bony socket and the same implant can be replanted into the bone cement packed bony socket.

3. To Treat Failing Implants and Restore Lost Bone from Peri-Implantitis

Failing implants from peri-implantitis which show abnormal bony loss and signs of infection can be treated with bone cement. A contaminated implant surface is de-toxificated with $H_2O_2$ for example, and bone cement is mixed and condensed into the bony defect around the ailing implant.

4. To Fill/Augment Bony Defects or Maxillary Sinus Requiring Bone Grafts Before/Simultaneously with Implant Placement Surgery When bone graft is required before the implant placement, bone cement can be used. For a direct sinus lift, a window of bone is created on the lateral wall of sinus, membrane is lifted carefully without tearing the membrane, implant with tapered healing abutment is placed immediately through the alveolar ridge and apex of the implants will penetrate into the sinus, bone cement is mixed and applied by condensing manner around the implant apexes, soft tissue flap is sutured back.

For an indirect sinus lift through the alveolar bone using osteotome and mallet, after initial drilling into the alveolar bone near the sinus floor, a series (from thinner to thicker) of osteotome is used to fracture the sinus floor and tent the membrane without perforation, bone cement is mixed and condensed into the bony socket and the cement is pushed, so the sinus membrane is lifted by the pressure gradually without tearing, leaving the bone cement only near the sinus floor area. The implant is self threaded into the bony socket.

For large vertical or horizontal bony defect areas that need block bone grafts, once an autogeous block bone is positioned into the defect and fixed with screws, the deficient gaps between the recipient bony site and the block bone graft can be filled by the bone cement.

5. To Fill the Space Between an Implant and an Extraction Socket

For immediate implant placement cases where an implant is placed immediately after a tooth extraction, a gap between the implant and extraction socket can be filled with the bone cement.

6. To Treat Failing Natural Teeth and Restore Lost Bone from Advanced Periodontitis Ailing natural teeth from periodontitis which show abnormal bony loss and signs of infection can be treated with bone cement. Granulation tissue in a defect is thoroughly cleaned, and a contaminated tooth surface is thoroughly cleaned. Bone cement is mixed and condensed into the bony defect around the ailing tooth.

7. Orthopedic Use

Whenever a bony defect needs to be filled in regions other than dental applications bone cements as described can be used.

While a number of embodiments of the invention are described, the above lists are not intended to be exhaustive. Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present invention. It is to be understood that the above description is intended to be illustrative and not restrictive. Combinations of the above embodiments, and other embodiments, will be apparent to those of skill in the art upon studying the above description.

What is claimed is:

1. A bone cement, comprising:
   an amount of Portland cement;
   an amount of calcium sulfate; and
   an amount of hydroxyethyl cellulose.
2. The bone cement of claim 1, wherein the amount of calcium sulfate is in a range between 10% and 35% of a dry weight of combined Portland cement and calcium sulfate.
3. The bone cement of claim 1, wherein the amount of calcium sulfate is in a range between 14% and 20% of a dry weight of combined Portland cement and calcium sulfate.
4. The bone cement of claim 1, wherein the amount of calcium sulfate is approximately 15% of a dry weight of combined Portland cement and calcium sulfate.
5. The bone cement of claim 1, further including an amount of water, and wherein the amount of hydroxyethyl cellulose is added to the amount of water in a range between 0.1% and 2.5% percent by water weight.
6. The bone cement of claim 1, further including an amount of water, and wherein the amount of hydroxyethyl cellulose is added to the amount of water in a range between 0.5% and 1.5% percent by water weight.
7. The bone cement of claim 1, further including an amount of water, and wherein the amount of hydroxyethyl cellulose is added to the amount of water in a range between 0.8% and 1.1% percent by water weight.
8. The bone cement of claim 1, further including a dispersed phase component.
9. The bone cement of claim 8, wherein the dispersed phase includes an amount of carbon fiber.
10. The bone cement of claim 9, wherein the amount of carbon fiber is in a range between 0.15% to 0.35% by dry weight.
11. The bone cement of claim 9, wherein the amount of carbon fiber is approximately 0.28 percent by dry weight.
12. A method, comprising:
    selecting an amount of water to provide a viscosity to match either a condensable application or an injectable application;
    adding the amount of water to dry components of a bone cement, the dry components including a mixture of Portland cement and calcium sulfate; and
    adding an amount of hydroxyethyl cellulose.
13. The method of claim 12, wherein adding an amount of hydroxyethyl cellulose includes adding an amount of hydroxyethyl cellulose to the water prior to adding the amount of water to the dry components.
14. The method of claim 12, further including adding an amount of a dispersed phase.

* * * * *